United States Patent [19]

Kriel

[11] Patent Number: 4,521,636

[45] Date of Patent: Jun. 4, 1985

[54] PREPARATION OF BIS(ALPHA-ALKYLBENZYL)ETHERS

[75] Inventor: Wayne A. Kriel, Westchester, Pa.

[73] Assignee: Atlantic Richfield Company, Los Angeles, Calif.

[21] Appl. No.: 562,365

[22] Filed: Dec. 16, 1983

[51] Int. Cl.³ .............................................. C07C 41/09
[52] U.S. Cl. .................................................... 568/659
[58] Field of Search ........................................ 568/659

[56] References Cited

U.S. PATENT DOCUMENTS

| | | | |
|---|---|---|---|
| 2,355,586 | 8/1944 | Perkins | 568/659 X |
| 2,366,203 | 1/1945 | Livak | 568/661 |
| 2,927,064 | 3/1960 | Luzader et al. | 568/659 X |
| 3,769,351 | 10/1973 | Mukai | 568/659 |

*Primary Examiner*—Bernard Helfin
*Attorney, Agent, or Firm*—Michael S. Jarosz

[57] ABSTRACT

Preparation of bis-(alpha-alkylbenzyl)ethers or substituted derivatives thereof by reaction at elevated temperature of the corresponding alpha alkylbenzyl alcohols in the presence of an aluminum sulfate treated calcined alumina catalyst, quenching of the catalyst and recovery of the desired ether by distillation following separation of the quenched catalyst, is disclosed. The alkyl methylbenzyl alcohol may be present as a component of an aromatic rich distill and product mixture derived from the ethyl benzene hydroperoxide epoxidation of an olefinically unsaturated compound.

15 Claims, No Drawings

PREPARATION OF BIS(ALPHA-ALKYLBENZYL)ETHERS

FIELD OF THE INVENTION

This invention relates to a process for the production of bis(alpha-alkylbenzyl)ethers, such as bis(alpha-methylbenzyl)ethers, by heating an alpha-alkyl benzyl alcohol, illustratively, alpha-methylbenzyl alcohol, ("MBA"), in the presence of an aluminum sulfate treated calcined alumina catalyst. The present application is especially concerned with the use of specified alumina catalysts in the etherification of an alpha methylbenzyl alcohol which is produced as a component of an epoxidation reaction product mixture obtained from the process for the production of an oxirane compound by the oxidation of ethylbenzene to produce an ethylbenzene hydroperoxide product mixture, followed by epoxidation of an olefinically unsaturated compound with said ethylbenzene hydroperoxide product mixture.

DESCRIPTION OF THE PRIOR ART AND BACKGROUND OF THE INVENTION

Bis(alpha-alkylbenzyl)ethers, such as bis(alpha-methylbenzyl)ether, have found application as dye carriers in the fabric industry, solvents in copying paper, and as direct substitutes for polychlorinated biphenyls in capacitors, and as heat transfer media, as well as components for use in the fragrance field. Certain of such ethers have also found use as pesticides, antioxidants, plastic additives and germicides. For example, Japanese Pat. No. 79-149900 has recently referred to the use of such ethers as electrical insulating oils and Japanese Pat. No. 79-136915 has referred to the use of such ethers in pressure-sensitive copying papers. The preparation of bis-(alpha-alkylbenzyl)ethers by reaction of a suitable alpha-unsubstituted or substituted phenylalkanol in the presence of a dehydrating agent, such as sulfuric acid, benzene-sulfonic acid, toluene sulfonic acid, and camphor-sulfonic acid, thereby splitting out water and forming an ether linkage between the aliphatic carbon atoms of two molecules of the original alkanol compound has been reported in the literature, for example, in U.S. Pat. No. 2,366,203 and *Journal of Organic Chemistry*, 28, 2914–5 (1963). More recently, as is disclosed in U.S. Pat. No. 4,299,996, a specific class of ion exchange resins containing acidic functionalities has been suggested for use in the preparation of such ethers from the corresponding alkanols. However, these catalysts, as well as those originally reported for use in the etherification reaction, suffer a combination of shortcomings, including poor selectivity to the desired bis ether, poor reproducibility of results and high costs.

Acid treatment is known to improve the properties of particulate, alumina-containing amorphous oxides for various uses such as absorption and as catalyst binders or supports. Treatment of alumina with acids will usually dissolve alumina in the acid phase and increase porosity and permeability and lower bulk density of the acid treated material. For example, U.S. Pat. No. 3,836,561 teaches that loss in structural stability caused by acid treatment of alumina containing amorphous refractory oxides is minimized by reacting the oxide with an acid in an aqueous medium at pH below about 5 in the presence of an ionizable salt soluble in the aqueous phase under conditions of temperature, pH and reaction time correlated with the reactivity of the acid and the oxide sufficient to react a portion of the alumina with the acid.

U.S. Pat. No. 3,997,476 discloses a process for increasing the pore volume of alumina by treating a calcined alumina with an organic acid, separating the acid-treated alumina from the acid solution by filtration or decantation, washing and drying the separated alumina in air or in a vacuum oven, and calcining the dried alumina at a temperature ranging from about 450° to about 550° C. for a period of time ranging from about 1 to 16 hours.

The refining of alpha-alkylbenzyl ethers, such as alpha-methylbenzyl ether, by distillation, such as azeotropic distillation, has also been reported in U.S. Pat. No. 2,927,064.

In one prior process for producing alkylene oxides, e.g. propylene oxide and styrene monomer, ethylbenzene is oxidized with air in a series of oxidizers to yield a solution of ethylbenzene hydroperoxide in ethylbenzene. During this oxidation, substantial quantities of methylbenzyl alcohol and acetophenone by-products are formed. This solution of ethylbenzene hydroperoxide is then concentrated in successive steps of distillation, and unreacted ethylbenzene is recycled for oxidation. In this process, ethylbenzene hydroperoxide is then typically used to epoxidize the olefinically unsaturated compound e.g. propylene, to propylene oxide, in the presence of a suitable catalyst, and the hydroperoxide itself is converted to methylbenzyl alcohol. By-products of this reaction include additional quantities of acetophenone, phenol, benzaldehyde, 2-phenylethanol, unreacted reactants and high boiling materials.

Excess propylene in the aforementioned propylene oxide epoxidation product is normally removed by distillation and propylene oxide may then be recovered by distillation as a crude product, leaving a stream comprising excess ethylbenzene, the aforementioned by-products and residues. The stream is then distilled to recover ethylbenzene overheads, leaving an aromatic rich distilland comprising methylbenzyl alcohol, acetophenone and a variety of other by-products, including aromatic alcohols. The composition of such distilland may vary widely and comprises a variety of alcohols, ketones and other by-products, as set forth in Table I, below.

In a typical propylene-oxide styrene monomer production process, the aforementioned methylbenzyl alcohol/acetophenone distilland (bottom stream) is purified through distillation, and then is fed through styrene production reactors where it is contacted in a liquid phase with a suitable dehydration catalyst to convert methylbenzyl alcohol to styrene. After removing styrene from the dehydration reaction product by distillation, there is produced an acetophenone-rich bottoms product which is then hydrogenated using a suitable catalyst to convert acetophenone to methylbenzyl alcohol, which may then be recycled for styrene production or employed in alternative applications. Further information concerning the production of alpha-methylbenzyl alcohol from such processes is described in U.S. Pat. No. 3,403,193.

Accordingly, it is the object of the present invention to provide a novel process for the preparation of bis-(alpha-alkylbenzyl)ethers.

Another object of this invention is to provide a process for the preparation of bis-(alpha-alkylbenzyl)ethers from alpha-alkylbenzyl alcohols by employing an aluminum sulfate treated calcined alumina catalyst which provides high reproducibility and selectivity to the desired ether.

Yet another object of the present invention involves the preparation of alpha-methylbenzyl ether while employing such treated alumina catalyst from a crude methylbenzyl alcohol-containing stream obtained in olefin oxide-styrene monomer production processes.

These and other objects of the present invention will become apparent from the following more detailed description and appended claims.

SUMMARY OF THE INVENTION

In accordance with the invention, bis(alpha-alkylbenzyl)ethers are produced by reacting an alpha-alkylbenzyl alcohol in the presence of an aluminum sulfate treated calcined alumina catalyst of specified characteristics under conditions which form a reaction product containing, in high yield, the desired bis(alpha-alkylbenzyl)ether. A major feature characteristic of the process of the present invention includes the quenching of the catalyst upon completion of the reaction, thereby precluding decomposition of desired bis ether product and high conversions of alcohol reactant over short reaction times while maintaining high selectivity to desired bis ether product.

It has now been discovered that the activity of alumina catalysts conventionally employed in dehydration reactions may be substantially increased, thereby rendering such catalyst suitable for use in etherification reactions by contacting a finely-divided calcined alumina with dilute aqueous solutions of aluminum sulfate and drying the treated alumina.

The aqueous treating solution contains from about 5 to 20 weight percent of aluminum sulfate (calculated as the hydrate, $Al_2(SO_4)_3.18H_2O$), preferably from about 7 to 12 weight percent. The aluminum sulfate may be added in either hydrated or anhydrous form, although the hydrated form is preferred. The weight ratio of aluminum sulfate (expressed as the hydrate) to calcined alumina in the treating solution (slurry) is generally within the range of from about 0.5:1 to about 2:1, and preferably is about 1:1. The ratio does not appear to be narrowly critical.

The contact treatment is effected at temperatures ranging from about 30° to 100° C., the upper limit of the temperature range being a function of the desire to maintain a liquid aqueous solution in the treating zone. The contacting of the alumina in the treating zone is effected for a time sufficient to facilitate penetration of the alumina particle core with the aqueous aluminum sulfate solution, and generally may range from about 10 min. to about 12 hours, the longer residence times being associated with the lower treatment temperatures. Preferably, the alumina is treated with the solution to a temperature within the range from about 50° C. to 100° C. for about 0.1 to 1 hour, with optimum results being attained at a temperature within the range from about 55° to 65° C. for 0.5 to 1 hour.

After the treatment, the alumina, optionally, may be washed with water to remove residual salt, and dried, to improve materials handling capabilities by heating at temperatures ranging from about room temperature to about 100° C., for a time sufficient, generally from about 15 minutes to 4 hours. Although the alumina to be treated according to the process of this invention must be precalcined, post-calcination is not necessary to obtain the enhanced characteristics of the catalyst employed in the process of this invention.

In accordance with one specific embodiment, commercially available technical grade, alpha-alkylbenzyl alcohols, such as methylbenzyl alcohol, are etherified in the presence of alumina sulfate treated calcined alumina catalysts to provide, in high yield commercially acceptable bis(alpha-alkylbenzyl)ethers.

In another specific embodiment, methylbenzyl alcohol present in a crude stream obtained from an olefin oxide/styrene monomer process, admixed with acetophenone, 2-phenylethanol, and a variety of other aromatic hydrocarbons and oxygenated derivatives thereof, is contacted with an aluminum sulfate treated calcined alumina catalyst under conditions which provide a high yield of bis(alpha-methylbenzyl)ether.

The ethers produced by the process of the present invention find particular use as dielectric fluids for capacitors and carbonless carbon paper solvents.

DETAILED DESCRIPTION OF THE INVENTION

The process of this invention is applicable to the production of bis(alpha-alkylbenzyl)ethers by etherification of alpha-alkylbenzyl alcohols. In general, the bis(alpha-alkylbenzyl)ethers capable of production in accordance with the process of the present invention correspond to the formula:

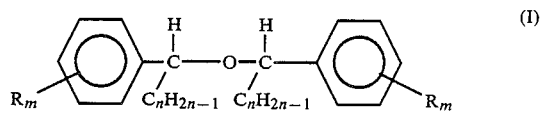

(I)

wherein R is the same or different lower alkyl of 1 to 6 carbon atoms, lower haloalkyl, bromo, chloro, sulfo or nitro; m is an integer not greater than 3 and n is an integer of from 1 to 7, inclusive. The desired ethers of the present invention are obtained by heating an alpha alkylbenzyl alcohol of the formula:

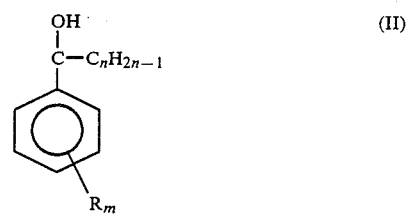

(II)

wherein R, m and n are as defined above. Exemplary of the alpha alkylbenzyl alcohols which are employed in preparing the desired ethers by the process of the present invention include, but are not limited to:
  alpha-methylbenzyl alcohol
  alpha-ethylbenzyl alcohol
  alpha-(4-chloro-phenyl)-ethanol
  alpha-(3,4,5-tribromo-phenyl)-ethanol
  alpha-(4-chloromethyl-phenyl)-ethanol
  alpha-(4-nitro-phenyl)-ethanol
  alpha-pentylbenzyl alcohol
  alpha-(4-bromo-phenyl)-hexanol
  alpha-(4-sulfo-phenyl)-ethanol
  alpha-(4-trifluoromethylphenyl)-ethanol
  alpha-hexylbenzyl alcohol
  alpha-propylbenzyl alcohol
and the like, and mixtures thereof.

In producing the bis(alpha-alkylbenzyl)ethers in accordance with the process of the present invention, the alpha-alkylbenzyl alcohol described is heated with agitation at a temperature below about 200° C., generally between about 125° C. and 175° C., and preferably between about 125° C. and 150° C. in the presence of the aluminum sulfated treated calcined alumina catalyst for a time sufficient to effect conversion of at least about 50% of said alcohol to the desired ether, thereby forming a reaction product mixture.

The etherification reaction may be carried out in the presence or absence of an inert solvent, such as an aromatic solvent, illustratively, benzene, toluene, acetophenone, or xylene.

As is above indicated, it is not necessary that the alpha-alkylbenzyl alcohol employed in the process of the present invention be a pure material. In this connection, an alternative embodiment of the invention resides in the use of an aromatic rich distilled comprising alpha-methylbenzyl alcohol, acetophenone and a variety of other by-products, including alcohols and ketones and other by-products obtained from the olefin oxide-styrene production process. The composition of a typical etherification feed obtained from the propylene oxide/styrene coproduction process is set forth in Table I below:

TABLE I

| Component | Weight (%) |
| --- | --- |
| alpha-phenylethanol | 75–85 |
| acetophenone | 10–20 |
| 2-phenylethanol | <5 |
| benzyl alcohol | <2 |
| benzaldehyde | <1 |
| cumylalcohol | <1 |
| phenol | <1 |
| cumene | <1 |
| ethylbenzene | <1 |

Water formed during the etherification reaction is removed as formed by distillation, or as an azeotropic mixture with the solvent, if employed, and if desired, its removal may be facilitated in conventional manner by the additional introduction of an inert gas, such as nitrogen, into the reaction system.

The catalysts employed in the process of the present invention are preferably in a finely-divided form so that they can be maintained in suspension with minimum agitation. Catalyst concentrations in the liquid phase reaction medium may range from about 0.1 to 20.0 weight percent, preferably from about 0.5 to about 3.0 weight percent.

The alumina treated according to the practice of this invention is an activated alumina having a surface area of at least 15, and preferably of about 40 to 250, square meters per gram as determined by the Brunauer-Emmett-Teller method, and preferably a high purity activated alumina such as that sold by Conoco under its "Catapal-SB" trademark. Alumina having low alkali and alkaline earth metal components as well as low iron contents are desired to minimize by-product formation. Aluminas having combined alkali and alkaline earth metal contents below aout 2000 ppm and iron contents below 2000 ppm are preferred. Alumina catalysts are activated by calcining the commercially available alumina at a temperature within the range from about 400° to 850° C. (preferably 400° to 600° C.) for a time within the range from about 0.5 to 24 hours.

In accordance with the process of the present invention, the etherification reaction is effected for a time sufficient, generally about 15 minutes to 4 hours, to effect conversion of at least about 50% of the alcohol reactant thereby forming a reaction product mixture. Following completion of the reaction, a basic compound is introduced into the reaction product mixture to deactivate the catalyst, i.e. convert the catalyst to an inert compound. The deactivated catalyst may be removed by conventional separating procedures, as by filtration, prior to recovery of the desired product. Any basic compound capable of neutralizing acidity of the catalyst may be employed. Illustrative suitable compounds employable for this purpose include alkali and alkaline earth metal hydroxides, carbonates or bicarbonates such as sodium hydroxide, sodium carbonate or sodium bicarbonate. Alternatively, ammonium or ammonium hydroxides or other salts, as well as organic amines such as alkyl amines, illustratively, triethylamine, may be employed for this purpose. It is critical, however, to employ the basic agent in slight excess of the amount sufficient to neutralize (i.e. be just above equivalence in acidity) the catalyst. Neutralization of the catalyst prevents decomposition of the desired ether product.

A variety of conventional methods, including distillation, extraction, or physical phase separation may be employed to recover the desired ether reaction product, unreacted starting materials, by-products, impurities, catalysts and diluents, if employed. In general, following removal of the catalyst, lower boiling unreacted starting materials are initially removed in a forecut, by distillation, followed by distillation of the desired ether product, which is carried out generally under vacuum.

The process of the present invention may be illustrated by the following examples. All parts and percents are based on weight. The reaction ratio and selectivities are calculated from analysis by Gas Chromotography.

This example describes the general experimental procedure used herein to produce bis(alpha-methylbenzyl)ether from pure alpha-methylbenzyl alcohol or a crude mixture, obtained from the propylene oxide/styrene process comprised described above, of 76.23 percent methylbenzyl alcohol 18.72 percent acetophenone, and 5.05 percent of other components described in Table I, above.

Into a 250 ml flask equipped with an agitator, a thermometer and a Dean-Stark condenser having a water-measuring tube, there is charged 100 parts of pure or crude alpha-methylbenzyl alcohol, as described, in each of a series of experiments. Thereafter, the indicated quantity of catalyst listed in following Table II is added thereto with stirring at the reaction temperature and the mixture is heated at these temperatures for the periods indicated. The catalyst is quenched upon completion of the reaction time indicated with a 29 weight percent aqueous potassium hydroxide solution and is removed by filtration before recovery of the bis(alpha methylbenzyl)ether from the reaction product mixture. Thereafter, the desired bis-alpha methylbenzyl ether is recovered from the reaction mixture of each Example by distillation at a temperature of 115°–122°/1 torr., following removal of unreacted methylbenzyl alcohol and styrene in a forecut at 75°–110°/1 torr. The results are set forth in Table II, below.

TABLE II

Synthesis of Bis(α-Methylbenzyl) Ether (BAMBE)

| Example | Feed | Catalyst | Temp. °C. | Reaction Time (hr) | Conversion mol % | Selectivity mol % | | |
|---|---|---|---|---|---|---|---|---|
| | | | | | | Styrene | BAMBE | Others |
| 1 | P[1] | Amberlyst ® 15[3] | 110–120 | 0.5 | 75.82 | 23.08 | 69.24 | 7.68 |
| 2 | C[2] | Amberlyst ® 15[3] | 115–127 | 0.5 | 76.28 | 32.56 | 63.44 | 4 |
| 3 | P[1] | Amberlyst ® 15[3] | 115–127 | 1 | 99.52 | 25.0 | 0.8 | 74.2 |
| 4 | P[1] | Alumina[4][6] | 130–135 | 0.75 | 73.4 | 4.2 | 91.1 | 4.7 |
| 5 | C[2] | Alumina[4][6] | 135–140 | 0.75 | 71.0 | 3.8 | 89.5 | 6.7 |
| 6 | C[2] | Alumina[5] | 135–150 | 0.75 | 36 | 38 | 32 | 30 |

[1]P = Pure Commercial Methyl Benzyl Alcohol, (98.5 weight percent)
[2]C = Crude Methyl Benzyl Alcohol, comprised of 76.23 weight percent MBA, 18.72 weight percent, Acetophenone, 5.05 weight percent others
[3]A polystyrene based heterogeneous sulfonic acid resin catalyst supplied by Rohm & Haas Company, charged in an amount of 1.0, percent of MBA present
[4]An alumina sulfate treated catalyst prepared by forming a slurry containing 10 percent by weight, of a finely-divided alumina in a 10 percent by weight, aqueous solution of $Al_2(SO_4)_3$ 18 $H_2O$, heating the slurry for 4 hours at 60° C., and drying the treated catalyst at ambient temperature for 1 hour, charged in an amount of 2.0 percent of MBA percent
[5]Untreated finely-divided calcined alumina, charged in an amount of 2.0% of MBA present hours charged in an amount of 2.0 percent of MBA present
[6]Catalyst quenched with 25 weight percent of KOH, based on the weight of catalyst employed (on a dry basis)

As is noted from Table II, high purity bis-(alpha methylbenzyl)ether is produced with little decomposition in accordance with Examples 4 and 5, illustrative of the process of the present invention; the product ether produced in these Examples is substantially odorless, and of high quality. As is further evident from the results set forth above, use of the Amberlyst and untreated alumina catalysts in the process results in a number of drawbacks, including high selectivity to undesired styrene and desirable by-products.

What is claimed is:

1. Process for the production of bis-(alpha-alkylbenzyl)ethers corresponding to the formula:

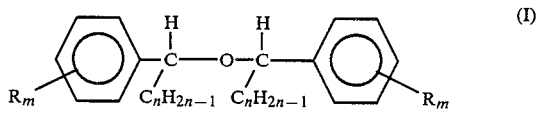 (I)

wherein, R is a member selected from the group consisting of lower alkyl, lower haloalkyl, chloro, bromo, sulfo and nitro radicals; m is an integer not greater than 3 and n is an integer of from 1 to 7, inclusive, comprising:

(a) heating, while removing water of dehydration as formed, an alpha alkylbenzyl alcohol of the formula:

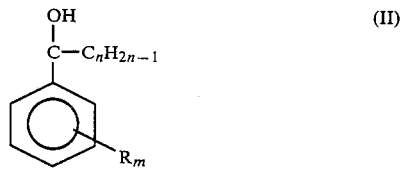 (II)

wherein, R, m and n are as defined above, with agitation, at a temperature below about 200° C. in the presence of an aluminum sulfate treated finely-divided calcined alumina catalyst present in catalytic amount, for a time sufficient to effect conversion of at least about 50% of said alcohol to the desired ether and thereby forming a reaction product mixture;

(b) introducing a basic compound to the reaction product mixture of Step (a), above, in an amount sufficient to deactivate the catalyst;

(c) separating the deactivated catalyst from the reaction mixture; and (d) recovering the desired bis(alpha-alkylbenzyl)ether from the reaction product mixture.

2. The process of claim 1 wherein said catalyst is present in an amount of between 0.1% and 20%, by weight, of said alcohol.

3. The process of claim 1 wherein said heating is carried out at a temperature of between about 125° C. and 150° C.

4. The process of claim 1 wherein heating of the alpha-alkylbenzyl alcohol is effected in an inert solvent.

5. The process of claim 4 wherein said inert solvent is an aromatic compound.

6. The process of claim 2 wherein m is 0 and n is 1 in each of said formulas.

7. The process of claim 2 wherein the alpha methyl benzyl alcohol starting material is present, in major proportion, as a component of an aromatic rich distilland product mixture derived from the ethyl benzene hydroperoxide epoxidation of an olefinically unsaturated compound.

8. The process of claim 1 wherein said catalyst is obtained by contacting a finely-divided calcined alumina with an aqueous solution containing from about 5 to 20 percent, by weight, of alumina sulfate, the weight ration of aluminum sulfate calculated as the hydrate, to calcined alumina in said aqueous solution being within the range from about 0.5 to about 2 said contacting being effected at a temperature within the range from about 30° C. to 100° C. for a time ranging from about 10 minutes to 12 hours.

9. The process of claim 8 wherein the contacting of the alumina with the aqueous solution of aluminum sulfate is effected at a temperature of between about 50° C. and 100° C. for a period ranging from about 0.1 to about 1 hour.

10. The process of claim 9 wherein the aqueous contacting solution contains from about 7 to about 12 percent by weight of aluminum sulfate.

11. The process of claim 10 wherein following the contacting with the aqueous aluminum sulfate solution, the alumina is dried by heating.

12. In the process for the production of bis(alpha-methylbenzyl)ether by heating an alpha methylbenzyl alcohol reactant in the presence of an acid catalyst at a temperature below about 200° C., followed by deactivation of the acidic catalyst by contact with a basic compound, separation of the deactivated catalyst, and recovery of the desired ether by distillation following removal of unreacted methyl benzyl alcohol and lower boiling impurities, the improvement which comprises:
 (a) employing, as reactant, an aromatic-rich distilland product mixture containing alpha-methylbenzyl alcohol in major proportion and, obtained from the ethyl benzene hydroperoxide epoxidation of an olefinically unsaturated compound.
 (b) employing, as said catalyst, a finely-divided calcined alumina obtained by contacting such alumina with an aqueous solution containing from about 5 to 20 percent, by weight, of aluminum sulfate, the weight ratio of aluminum sulfate, calculated as the hydrate, to calcined alumina in said aqueous solution being withn the range from about 0.5 to about 2, said contacting being effected at a temperature within the range from about 30° C. to 100° C. for a time ranging from about 10 minutes to 12 hours.

13. The process of claim 12 wherein said alumina catalyst is obtained by contacting finely-divided calcined alumina with an aqueous solution from about 7 to about 12 percent, by weight, of aluminum sulfate, and said contacting is effected at a temperature within the range from about 50° C. to 100° C. for a time ranging from about 0.1 to 1 hours.

14. The process of claim 13 wherein following the contacting with the aqueous aluminum sulfate solution, the alumina is dried by heating.

15. The process of claim 14 wherein the alumina is worked to remove residual aluminum sulfate before drying.

* * * * *